United States Patent [19]

Richards et al.

[11] 4,238,142
[45] Dec. 9, 1980

[54] METHOD AND APPARATUS FOR EXAMINING AND PHOTOGRAPHING THE OCULAR FUNDUS

[75] Inventors: William Richards, Medway; Bernard Grolman, Worcester; Joseph W. Kantorski, Southbridge, all of Mass.

[73] Assignee: American Optical Corporation, Southbridge, Mass.

[21] Appl. No.: 970,304

[22] Filed: Dec. 18, 1978

[51] Int. Cl.³ .............................. A61B 6/10; A61B 3/14; G03B 29/00
[52] U.S. Cl. ......................................... 351/7; 351/14; 351/16; 351/39; 354/62
[58] Field of Search .................... 354/62; 351/6, 7, 13, 351/16, 14, 39; 350/205, 206, 266

[56] References Cited

U.S. PATENT DOCUMENTS

| 3,843,240 | 10/1974 | Cornsweet | 351/14 |
| 3,915,564 | 10/1975 | Urban | 354/62 X |
| 4,132,466 | 1/1979 | Matsumura | 351/7 |

Primary Examiner—John K. Corbin
Assistant Examiner—Rodney B. Bovernick
Attorney, Agent, or Firm—Jeremiah J. Duggan; Alan H. Spencer

[57] ABSTRACT

An instrument for photographing the ocular fundus is aligned by using a physical aperture designed to permit illumination of only a small area of the optic disc for minimal patient awareness of incident light and corresponding pupil dilation without mydriatics. The increased field of view and obliquity of viewing afforded by pupil dilation permits flashing of the fundus for photographic recording without image obscuring corneal reflections. The light restricting aperture is removed immediately before photographic recording.

7 Claims, 3 Drawing Figures

METHOD AND APPARATUS FOR EXAMINING AND PHOTOGRAPHING THE OCULAR FUNDUS

BACKGROUND OF THE INVENTION

1. Field of the Invention

Ophthalmic examining and photographic recording instruments with particular reference to means and method for achieving substantial pupil dilation for large field viewing of the fundus and increased obliquity of instrument alignment.

2. Discussion of the Prior Art

In viewing or photographing the ocular fundus the patient's normal pupil, acting as a field stop, limits the extent of the fundus available for any given angle of inspection.

In order to facilitate relatively easy, wider field inspection, mydriatic agents have been used where permitted by law. Their use is not casually employed since there are attendant risks. At the least, the patient is handicapped with blurred vision for relatively long periods and old posterior synechia may be torn and the crystalline lens absorbed.

Optical alignment of a fundus camera with invisible light in a darkened environment which promotes pupil dilation without mydriatics similarly handicaps the patient with prolonged blurred vision after photographic flashing, not to mention the attending traumatism of receiving a high intensity photoflash while accommodated to darkness.

It is, accordingly, an object of the present invention to achieve pupil dilation with minimal patient awareness or discomfort after photoflashing of the fundus whereby increased obliquity of viewing of the fundus may be accomplished for wide field inspection and displacement of corneal reflected image from the recording field.

Another object is to provide means and method for illuminating only a small area of the light-insensitive optic disc for effecting the aforesaid pupil dilation.

Other objects and advantages of the invention will become apparent from the following description.

SUMMARY OF THE INVENTION

The foregoing objects and their corollaries are accomplished without the use of chemical agents by the introduction into a beam of examining light (e.g. from a halogen lamp) of a physical aperture which reduces the incident bundle diameter so that only a small area of the optic disc is illuminated. Because there are no retinal light receptors present in the disc area, the patient's minimal awareness arises only from light scattered by the disc and pupil dilation takes place.

The patient's normal pupil which acts as a field stop limiting the extent of fundus available for any given angle of inspection is thus expanded for wide field examination and increased obliquity of operator viewing. The latter effects displacement of the image of obscuring corneal reflections away from the field of view to be photographically recorded.

Mechanical linkages are provided to remove the light restricting aperture immediately before the fundus is flashed for photographic recording.

Details of the invention will become more readily apparent from the following description when taken in conjunction with the accompanying drawings, in which.

DESCRIPTION OF THE PREFERRED EMBODIMENTS

Figure 1:
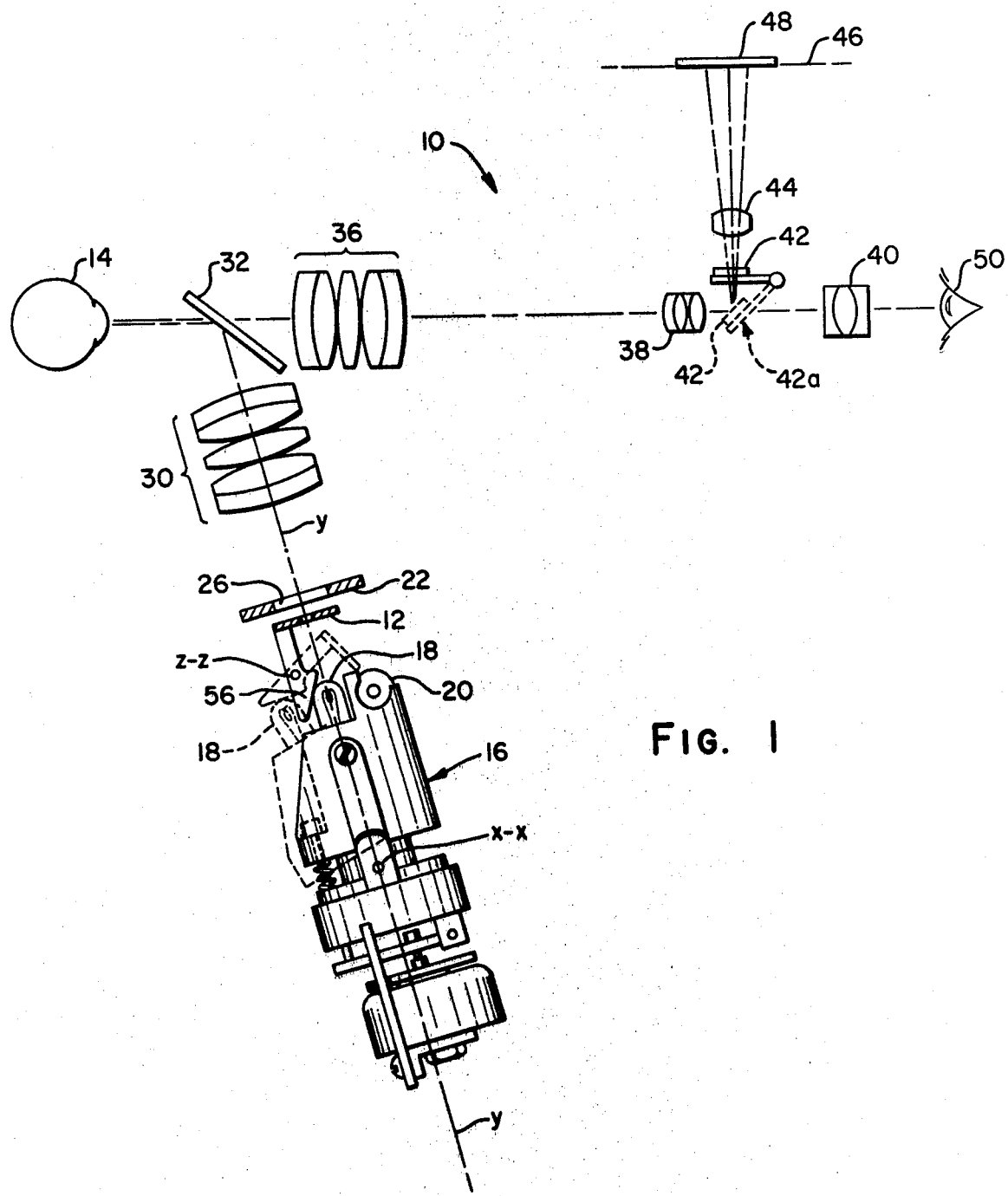
FIG. 1 is a diagramatic illustration of an ocular fundus examining and photographic system incorporating the present invention.

The system 10 of FIG. 1 is exemplary of ocular fundus examining and photographing instrumentation into which a physical aperture, i.e. stop 12, may be incorporated according to this invention for illuminating only a small portion of the fundus of a patient's eye 14.

System 10 comprises illuminator 16 having incandescent (e.g. halogen) lamp 18 and flashtube 20 which may embody a strobe lamp for selectively emitting a high intensity flash of light when electrically triggered.

Illuminator 16 is pivotable about axis x—x for selectively bringing first one of lamps 18 and 20 and then the other to alignment with axis y—y of the light input section of system 10. Axis x—x is perpendicular to the sheet of drawings.

Those requiring further details of the structure and operation of illuminator 16 may refer to copending application Ser. No. 894,226 now U.S. Pat. No. 4,184,752 which was filed on Apr. 7, 1978.

Beyond illuminator 16 and stop 12 is iris diaphragm 22 (FIGS. 1-3) having lever 24 for opening and closing aperture 26. Diaphragm 22 is mounted conventionally in the handle 28 (FIGS. 2, 3) of a hand-held ophthalmic instrument such as, for example, an ophthalmoscope fitted with a fundus camera and having mirror and lens optical components generally of the type and arrangement of system 10. It is to be understood that system 10 represents but one of several forms of apparatuses to which the present invention has applicability.

System 10 further includes multiple lens component 30 (FIG. 1) for receiving and directing light from illuminator 16 along axis y—y to beam splitter 32 for reflection into the eye 14 under examination. Portions of this light reflected from within eye 14, i.e. by its fundus, and passing through beamsplitter 32 are imaged by objective 36 forewardly thereof. This image is erected by lenses 38 and viewed with eyepiece 40.

A mirror 42 movable to the position illustrated by broken lines 42a may be selectively employed to focus the image of the fundus of eye 14 through camera lens 44 onto film plane 46 for photographic recording upon film 48. When in the position of full line illustration, mirror 42 provides a closure for the camera aperture to protect film 48 from unwanted exposure. With the instrument system 10 placed in the illustrated eye-examining mode where a practitioner's eye 50 may view images of the patient's eye 14, e.g. its fundus, for screening or photographic alignment purposes, illuminator 16 is pivoted to the position illustrated in FIG. 1. This brings incandescent lamp 18 into alignment with axis y—y to provide constant illumination of eye 14.

Figure 2:
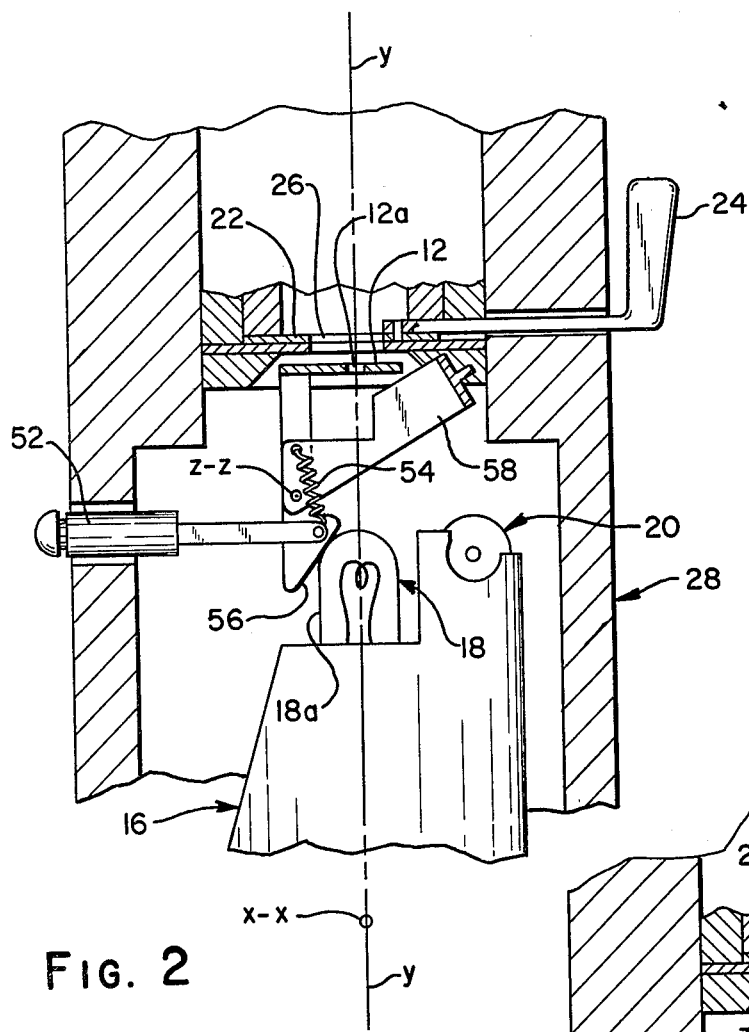
FIG. 2 is an enlarged fragmentary and partially cross-sectioned illustration of details of a preferred embodiment of the invention.

When preparing to photograph the fundus of eye 14, diaphragm 22 may be fully opened and optical stop 12 is brought into the position of full line illustration in FIGS. 1 and 2, i.e. by pressing button 52 into handle 28 toward lamp 18. Overriding spring 54 fixes stop 12 above lamp 18 with its depending cam portion 56 disposed against the envelope 18a of lamp 18.

Stop 12, having an aperture 12a of approximately 1.5 mm in diameter, reduces the size of the bundle of light reaching eye 14 to only a small area of the optic disc when instrument system 20 is properly aimed and focused thereat for photographic recording purposes.

Because of no retinal light-receptors being present in the disc area of the fundus and the patient's minimal awareness of only light scattered by the disc, natural pupil dilation takes place when system 10 is used in subdued light.

With pupil dilation, the angle of view of the fundus of eye 14 is expanded for wide field inspection and increased obliquity of viewing. The latter, in particular, effects displacement of reflected images of the cornea of eye 14 away from the field of view desired to be photographed.

From the foregoing, it can be seen that system 10, with stop 12 in place, is especially adapted to aligning, focusing and photographing the area of the fundus which lies in the vicinity of the optic disc. The disc area illuminated need only be large enough for the operator to maintain focus.

Figure 3:
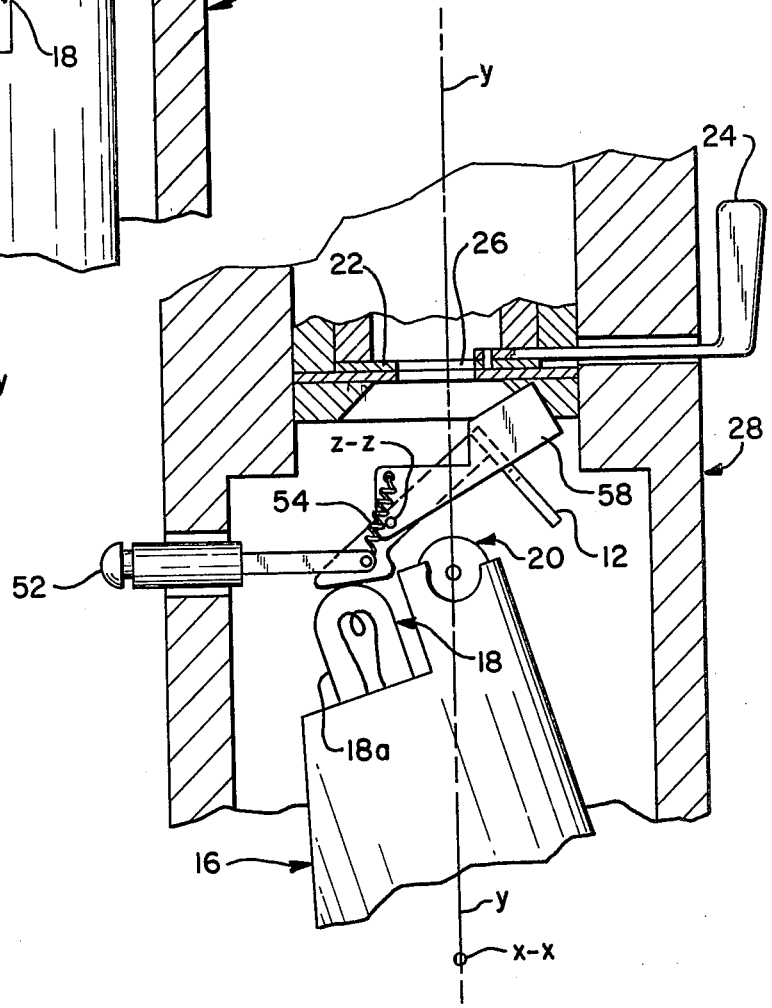
FIG. 3 is a view similar to FIG. 2 but illustrating light-restricting aperture mechanism as being displaced to permit unrestricted photoflashing of the ocular fundus according to the invention.

With alignment and focusing completed as described above, illuminator 16 is tilted about axis x—x to the position illustrated by broken lines in FIG. 1 and full lines in FIG. 3.

This tilting of illuminator 16, with lamp 18 engaging cam portion 56 of stop 12, swings stop 12 away from diaphragm 22 and brings strobe lamp 20 into alignment with axis y—y for a photo-flashing of the fundus of eye 14.

Bracket 58 (FIGS. 2 and 3) supports stop 12 which pivots about axis z—z. Axis z—z is perpendicular to the sheet of drawings.

Overriding spring 54 retains stop 12 in the aforesaid out-of-the-way position.

With instrument 10 in readiness for photoflashing, which takes place instantaneously with alignment of strobe lamp 20 on axis y—y, mirror 42 is simultaneously moved to the position illustrated with broken lines in FIG. 1. This opens the camera aperture and exposes film 48 to light returning from eye 14.

The foregoing sequence of operations, i.e. relating to the operation of illuminator 16 and mirror 42, is described in detail in the aforementioned copending application Ser. No. 894,226.

After photoflashing, illuminator 16 is again pivoted about axis x—x to return incandescent lamp 18 to its original alignment with axis y—y. Mirror 42 simultaneously swings back toward camera lens 44 closing the camera aperture.

Overriding spring 54 retains stop 12 in the previously mentioned out-of-the-way position until again manually moved by depression of button 52. Thus, until stop 12 is selectively manually moved back into alignment with axis y—y, system 10 remains in a conventional eye-examining mode wherewith the practitioner may adjust diaphragm 22 with lever 24 at will and without interference from stop 12.

Those skilled in the art will readily appreciate that various other modifications and adaptations of the precise form of the invention here shown may be made to suit particular requirements. It is, accordingly, intended that all modifications which incorporate the novel concept disclosed are to be construed as coming within the scope of the claims or the range of equivalency to which they are entitled.

We claim:

1. In the system of an ophthalmic photographic recording instrument including means for directing light along a given path into an eye for illumination of its fundus and means for viewing the illuminated fundus to align and focus said instrument thereupon, the improvement comprising the combination in said means for directing light into said eye of:

incandescent and photoflash lamp means alternately individually positionable in said given path to direct light emitted therefrom into said eye for respectively viewing said fundus and photographing same;

an optical stop having an aperture with a diameter smaller than the approximate diametral size of the optic disc of said eye to be illuminated and selectively positionable in said given path between said incandescent lamp means and eye when said incandescent lamp means is positioned in said path, said stop being movable away from said given path when said photoflash lamp is positioned in said path thereby permitting direct exposure of said eye to light emitted from said photoflash lamp when activated;

means for moving said optical stop into said given path when said incandescent lamp is positioned in said path; and means for moving said optical stop away from said path when said photoflash lamp is positioned in said path.

2. The improvement in an ophthalmic photographic recording instrument according to claim 1 wherein said means for moving said optical stop into said given path includes a push button connected to said stop.

3. The improvement in an ophthalmic photographic recording instrument according to claim 1 wherein said means for moving said optical stop away from said path includes a cam on said stop adapted to be engaged by said incandescent lamp for effecting said movement away from said path simultaneously with movement of said incandescent lamp away therefrom and positioning of said photoflash lamp in said path.

4. The improvement in an ophthalmic photographic recording instrument according to claim 1 including a bracket supporting said optical stop, said stop being pivotally connected to said bracket and overriding spring means fixing said stop alternately at said position in said given path and away therefrom respectively when said incandescent and photoflash lamps are brought into said path.

5. The method of causing dilation of an eye for wide field and obliquity of viewing and photographing of the fundus comprising the steps of:

providing means for selectively alternatively directing continuous and relatively high intensity photoflash light into said eye;

optically stopping said continuous light to a bundle size less than the diametral size of the optic disc of the fundus of said eye;

aligning said bundle of light with said disc to effect incidence of said bundle approximately centrally of said disc for substantial insensitivity of said eye to said incidence of light and consequent dilation of the pupil thereof;

aligning camera means obliquely toward said disc through said dilated pupil; and thereafter directing said high intensity photoflash light into said eye for photorecording with said camera means.

6. In the system of an ophthalmic photographic recording instrument including means for directing light along a given path into an eye for illumination of its fundus and means for viewing the illuminated fundus to align and focus said instrument thereupon, the improvement comprising the combination in said means for directing light in said eye of:

incandescent and photoflash lamp means alternately individually positionable in said given path to direct light emitted therefrom into said eye for respectively viewing said fundus and photographing same;

an optical stop having an aperture diameter smaller than the approximate diametral size of the optical disc of said eye to be illuminated, said aperture diameter being approximately 1.5 mm and selectively positionable in said given path between said incandescent lamp means and eye when said incandescent lamp means is positioned in said path, said stop being movable away from said given path when said photoflash lamp is positioned in said path thereby permitting direct exposure of said eye to light emitted from said photoflash lamp when activated;

means for moving said optical stop into said given path when said incandescent lamp is positioned in said path; and means for moving said optical stop away from said path when said photoflash lamp is positioned in said path.

7. The method of causing dilation of an eye for wide field and obliquity of viewing and photographing of the fundus comprising the steps of:

providing means for selectively alternatively directing continuous and relatively high intensity photoflash light into said eye;

optically stopping said continuous light to a bundle size less than the diametral size of the optic disc of the fundus of said eye, said bundle diameter being approximately 1.5 mm;

aligning said bundle of light with said disc to effect incidence of said bundle approximately centrally of said disc for substantial insensitivity of said eye to said incidence of light and consequent dilation of the pupil thereof;

aligning camera means obliquely toward said disc through said dilated pupil; and thereafter directing said high intensity photoflash light into said eye for photorecording with said camera means.

* * * * *